(12) United States Patent
Ericson

(10) Patent No.: US 10,537,097 B2
(45) Date of Patent: Jan. 21, 2020

(54) METHODS FOR TREATING RED BLOOD CELLS

(71) Applicant: VIACELL, LLC., Ham Lake, MN (US)

(72) Inventor: Daniel G. Ericson, Rochester, MN (US)

(73) Assignee: Viacell, LLC, Ham Lake, MN (US)

( * ) Notice: Subject to any disclaimer, the term of this patent is extended or adjusted under 35 U.S.C. 154(b) by 0 days.

(21) Appl. No.: 15/401,732

(22) Filed: Jan. 9, 2017

(65) Prior Publication Data

US 2017/0251660 A1    Sep. 7, 2017

Related U.S. Application Data

(63) Continuation of application No. 13/028,819, filed on Feb. 16, 2011, now abandoned.

(60) Provisional application No. 61/338,299, filed on Feb. 16, 2010.

(51) Int. Cl.
| | |
|---|---|
| *A01N 1/02* | (2006.01) |
| *A61K 31/19* | (2006.01) |
| *A61K 31/7004* | (2006.01) |
| *A61K 31/7052* | (2006.01) |
| *A61K 31/7068* | (2006.01) |
| *A61K 33/42* | (2006.01) |
| *A61K 35/18* | (2015.01) |

(52) U.S. Cl.
CPC ........... *A01N 1/0226* (2013.01); *A61K 31/19* (2013.01); *A61K 31/7004* (2013.01); *A61K 31/7052* (2013.01); *A61K 31/7068* (2013.01); *A61K 33/42* (2013.01); *A61K 35/18* (2013.01)

(58) Field of Classification Search
None
See application file for complete search history.

(56) References Cited

U.S. PATENT DOCUMENTS

| | | | |
|---|---|---|---|
| 3,847,738 A | 11/1974 | Brake et al. | |
| 4,386,069 A | 5/1983 | Estep | |
| 4,432,750 A | 2/1984 | Estep | |
| 4,572,899 A | 2/1986 | Walker et al. | |
| 4,585,735 A | 4/1986 | Meryman et al. | |
| 4,675,185 A | 6/1987 | Kandler et al. | |
| 4,695,460 A | 9/1987 | Holme | |
| 4,710,532 A | 12/1987 | Hull et al. | |
| 4,769,318 A | 9/1988 | Hamasaki et al. | |
| 4,774,088 A | 9/1988 | Vora | |
| 4,812,310 A | 3/1989 | Sato et al. | |
| 4,853,370 A | 8/1989 | Ecanow et al. | |
| 4,870,002 A | 9/1989 | Kiel | |
| 4,880,786 A | 11/1989 | Sasakawa et al. | |
| 4,889,943 A | 12/1989 | Kawamura et al. | |
| 4,961,928 A | 10/1990 | Holme et al. | |
| 5,248,506 A | 9/1993 | Holme et al. | |
| 5,250,303 A | 10/1993 | Meryman et al. | |
| 5,487,971 A | 1/1996 | Holme et al. | |
| 5,601,972 A | 2/1997 | Meryman | |
| 5,769,839 A | 6/1998 | Carmen et al. | |
| 5,789,151 A | 8/1998 | Bitensky et al. | |
| 5,906,915 A | 5/1999 | Payrat et al. | |
| 6,150,085 A | 11/2000 | Hess et al. | |
| 6,159,942 A | 12/2000 | St. Cyr et al. | |
| 6,447,987 B1 | 9/2002 | Hess et al. | |
| 7,448,606 B1 | 11/2008 | Johnson | |
| 7,687,468 B2 | 3/2010 | St. Cyr et al. | |
| 8,980,542 B2 * | 3/2015 | Ericson | A01N 1/0226 435/2 |
| 10,412,957 B2 * | 9/2019 | Ilyin et al. | A01N 1/0263 |
| 2003/0148256 A1 | 8/2003 | Payrat et al. | |
| 2004/0106094 A1 | 6/2004 | Payrat et al. | |
| 2004/0192553 A1 | 9/2004 | Kurauchi et al. | |
| 2005/0074743 A1 | 4/2005 | Purmal et al. | |
| 2005/0208462 A1 | 9/2005 | Bitensky et al. | |
| 2006/0292134 A1 | 12/2006 | Stohs | |
| 2007/0111191 A1 | 5/2007 | St. Cyr et al. | |
| 2007/0178434 A1 | 8/2007 | Natan et al. | |
| 2007/0298406 A1 | 12/2007 | Martorell Pena et al. | |
| 2009/0239208 A1 | 9/2009 | Mayaudon et al. | |
| 2011/0256522 A1 | 10/2011 | Ericson et al. | |

FOREIGN PATENT DOCUMENTS

| | | | |
|---|---|---|---|
| DE | 37 11 699 A1 | | 11/1988 |
| EP | 1869977 A1 | | 12/2007 |
| GB | 1044649 | * | 10/1966 |
| JP | 61012626 A | | 1/1986 |
| WO | WO 2004/105483 | * | 12/2004 |
| WO | WO 2004/105483 A1 | | 12/2004 |
| WO | WO 2006/088455 A1 | | 8/2006 |
| WO | WO 2011/103177 A1 | | 8/2011 |

(Continued)

OTHER PUBLICATIONS

Prankerd T. et al. Revival of Stored Blood with Guanosine. The Lancet 267(6921)469-471 Apr. 21, 1956. (Year: 1956).*
Whittam R. The Support of Active Potassium Transport in Human Red Cells by Nucleosides and Deoxynucleosides. J Physiology 154(3)608-613, Dec. 1960.*
U.S. Appl. No. 61/598,613, filed Feb. 14, 2012.
"Acid-citrate-dextrose," [online]. Wikipedia, the free encyclopedia, [retrieved on Jun. 16, 2010]. Retrieved from the Internet: <URL:http://en.wikipedia.org/wiki/Acid-citrate- dextrose>; 2 pgs; last modified Apr. 11, 2010.
Akerblom et al., "Restoration of Defective Oxygen-transport Function of Stored Red Blood Cells by Addition of Inosine," *Scand. J Clin. Lab. Invest.*, 1968; 21(3): 245-8.

(Continued)

*Primary Examiner* — Ralph J Gitomer
(74) *Attorney, Agent, or Firm* — Mueting, Raasch & Gebhardt, P.A.

(57) ABSTRACT

Methods for storing or rejuvenating blood involve contacting blood with a blood storage composition or a blood rejuvenating composition that include D-ribose and a nucleoside other than inosine (e.g., guanosine).

20 Claims, No Drawings

(56) References Cited

FOREIGN PATENT DOCUMENTS

WO    WO 2011/103179 A1    8/2011

OTHER PUBLICATIONS

"Anticoagulation and Preservation" [online]. Bloodindex, [retrieved on Jun. 16, 2010]. Retrieved from the Internet: <URL: http://www.bloodindex.net/blood anticoagulation_preservation.php>; 4 pgs.
Arun et al.; "Decreased Hemolysis and Lipid Peroxidation in Blood during Storage in the Presence of Nicotinic Acid," Vox Sang., 1999; 76(4): 220-5.
Bartlett et al., "Changes in the Phosphate Compounds of the Human Red Blood Cell During Blood Bank Storage," J Clin. Invest., Jan. 1960; 39(1): 56-61.
Becker, "Phosphoribosylpyrophosphate synthetase and the regulation of phosphoribosylpyrophosphate production in human cells," Prag. Nucleic Acid Res. Mol. Biol., 2001; 69: 115-48.
Beutler et al., "The in vivo regeneration of red cell 2,3-diphosphoglyceric acid (DPG) after transfusion of stored blood," J. Lab. Clin. Med., Aug. 1969; 74(2): 300-4.
"Blood components," [online]. Diaglab, Cornell University [retrieved on Jun. 15, 2010]. Retrieved from the Internet: <URL: http:www.diaglab.vet.cornell.edu/clinpath/modules/coags/comp.htm>; 3 pgs.
"Blood FAQ," American Association of Blood Banks [online]. [retrieved on Aug. 18, 2011]. Available online:<URL: http://www.aabb.org/resources/bct/pages/bloodfaq.aspx,> 3 pgs.
Bunn et al., "Hemoglobin Function in Stored Blood," J Clin. Invest., Feb. 1969; 48(2): 311-21.
Chen et al., "Solubility Enhancement of Nucleosides and Structurally Related Compounds by Complex Formation," Pharm. Res., Mar. 1994; 11(3): 398-401.
Chiu et al., "Lipid peroxidation in human red cells," Semin. Hematol., Oct. 1989; 26(4): 257-76.
"Circular of Information: For the Use of Human Blood and Blood Components," American Association of Blood Banks et al., Aug. 2009, revised Dec. 2009:40 pgs.
Corwin et al., "The CRIT Study: Anemia and blood transfusion in the critically ill—Current clinical practice in the United States," Crit. Care Med., 2004; 32(1): 39-52.
Dawson et al., "Blood Preservation XXIX, Pyruvate Maintains Normal Red Cell 2.3-DPG for Six Weeks of Storage in CPD-Adenine," Transfusion, Mar.-Apr. 1980; 20(2): 218-223.
Dawson et al., "Blood Preservation 33. Phosphate enhancement of ribose maintenance of 2,3-DPG and ATP," Transfusion, Mar.-Apr. 1981 ; 21(2): 215-8.
Dawson et al., "Blood preservation 42: improvement of ascorbate's ability to maintain 2,3-DPG with inosine," Transfusion, May-Jun. 1981 ; 21(3): 285-90.
Dawson et al., Blood preservation 50: Red Cell 2,3 DPG Maintenance in CPD-Adenine Stored Blood by Several Mechanisms, The Red Cell: 5$^{th}$ Annual Arbor Conf., 1981:643-660.
Dawson, "Preservation of red blood cells for transfusion," Hum. Pathol., Mar. 1983; 14(3): 213-7.
Dawson et al., "Dihydroxyacetone, pyruvate, and phosphate effects on 2,3 DPG and ATP in citrate-phosphate-dextrose-adenine blood preservation," Transfusion, Jul.-Aug. 1984 ; 24(4): 327-9.
Dawson et al., "Control of red cell 2,3-DPG levels in vitro and a proposal for in vivo control in response to hypoxia and metabolic demand," Prog. Clin. Biol. Res., 1985; 195: 349-68.
Delivoria-Papadopoulos et al., "Oxygen-hemoglobulin dissociation curves: effect of inherited enzyme defects of the red cell," Science, Aug. 8, 1969; 165(893): 601-2.
Deneke et al., "Regulation of cellular glutathione," Am. J Physiol. Lung Cell. Mol. Physiol., 1989; 257: L163-73.
Department of Health and Human Services, Food and Drug Administration, "REJUVESOLO®, Red Blood Cell Processing Solution," enCyte™ Systems, Inc.; 32 pages. Oct. 5, 1998.

Dormandy, "The autoxidation of red cells," Br. J. Haematol, May 1971; 20(5): 457-61.
Dumaswala et al., "Glutathione loading prevents free radical injury in red blood cells after storage," Free Rad. Res., Nov. 2000; 33(5): 517-29.
Dumaswala et al., "Glutathione protects chemokine-scavenging and antioxidative defense functions in human RBCs," Am. J Physiol. Cell Physiol., 2001; 280(4): C867-73.
Elfath, "Is it time to focus on preserving the functionality of red blood cells during storage?" Transfusion, Sep. 2006; 46:1469-70.
Fitzgerald et al., "Transfusing red blood cells stored in citrate phosphate dextrose adenine-I for 28 days fails to improve tissue oxygenation in rats," Crit. Care Med., May 1997; 25(5): 726-32.
"FDA Licensure for Conversion to CP2D/AS-3 Anticoagulant/Additive Systems," Pall Corporation, East Hills, NY, 2004, 22 pgs.
"Guanosine," from Wikipedia, the free encyclopedia, retrieved from the internet at <http://en.wikipedia.org/wiki/Guanosine>, retrieved on Sep. 13, 2013; 2 pgs.
Halliwell et al., "Oxygen toxicity, oxygen radicals, transition metals and disease," Biochem. J, Apr. 1984; 219(1): 1-14.
Harris et al., "Blood Manufacturing: Component Preparation, Storage, and Transportation," Blood banking and transfusion medicine: basic principles and practice, Hillyer et al. eds, Chapter 12, Elsevier, London, England, 2007; pp. 183-203.
Hawkes et al., "Heart surgery patients put in danger by using 14-day-old blood," TimesOnline (London), Mar. 24, 2008 [retrieved on Oct. 13, 2008].Retrieved from the Internet:<URL:http://www.timesonline.co.uk/tol/life_and_style/health/article3607486>; 2pgs.
Hébert et al., "A Pilot Trial Evaluating the Clinical Effects of Prolonged Storage of Red Cells," Anesth. Analg., May 2005; 100(5): 1433-8.
Hess et al., "Buffering and dilution in red blood cell storage," Transfusion, Jan. 2006; 46:50-54.
"Inosine," [online]. Wikipedia, the free encyclopedia, [retrieved on Feb. 11, 2010]. Retrieved from the Internet: <URL: http://en.wikipedia.org/wiki/Inosine>; 3 pgs.
International Search Report and Written Opinion of the International Searching Authority dated Apr. 5, 2011, International Application No. PCT/US2011/025066, filed Feb. 16, 2011, 10 pgs.
Jain, "Evidence for membrane lipid peroxidation during the in vivo aging of human erythrocytes," Biochim. Biophys. Acta, Jan. 1988; 937(2): 205-10.
Jensen, "Red blood cell pH, the Bohr effect, and other oxygenation-linked phenomena in blood $O_2$ and $CO_2$ transport," Acta Physiol. Scand., Nov. 2004; 182(3): 215-27.
Jóźwik et al., "Antioxidant defence of red blood cells and plasma in stored human blood," Clin. Chim. Acta, Nov. 28, 1997; 267(2): 129-42.
Kanias et al., "Biopreservation of red blood cells—the struggle with hemoglobin oxidation," FEES J, Jan. 2010; 277(2): 343-56. Available online Nov. 26, 2009
Koch et al., "Duration of Red-Cell Storage and Complications After Cardiac Surgery," N. Engl. J Med., Mar. 20, 2008; 358:1229-1239.
Knight et al., "Lipid peroxidation in stored red cells," Transfusion, May 1992; 32(4): 354-7.
Marik et al., "Effect of stored-blood transfusion on oxygen delivery in patients with sepsis," JAMA, Jun. 16, 1993; 269(23): 3024-9.
Material Safety Data Sheet, Fenwal, 4368, Version 2, Print date: Jan. 14, 2011, 5 pgs.
McCullough, Transfusion Medicine, 2$^{nd}$ edition, Elsevier, London, England, 2005.
Medline Abstract, 75128511, Petrich et al., "Influence ofribose on 2,3-diphosphoglycerate concentrations in human erythrocytes," 1975: 1 pg.
Moore, "Long-Term Storage and Preservation of Red Blood Cells," Biotechnology of Blood, Stoneham, MA, Chap. 2:31-46.
"Nucleoside," [online]. Wikipedia, the free encyclopedia, [retrieved on Feb. 11, 2010]. Retrieved from the Internet: <URL: http://en/wikipedia.org/wiki/Nucleoside>; 2 pgs; last modified Feb. 10, 2010.
Oski et al., "The In Vitro Restoration of Red Cell 2,3-Diphosphoglycerate Levels in Banked Blood," Blood, Jan. 1971; 37(1): 52-8.

(56) References Cited

OTHER PUBLICATIONS

Petrich et al., "Der Einfluss von Ribose auf die 2,3-Diphosphoglycerat-Konzentration menschlicher Erythrozyten," *Blut*, 1995; 30:175-182. (English translation included (12 pgs)).

Raat et al., "The effect of storage time of human red cells on intestinal microcirculatory oxygenation in a rat isovolemic exchange model," *Crit. Care Med.*, Jan. 2005; 33(1): 39-45.

"Ribose 5-phosphate," from Wikipedia, the free encyclopedia, retrieved from the internet at <http://en.wikipedia.org/wiki/Ribose_5-phosphate>, retrieved on Sep. 13, 2013; 1 pg.

Simon et al. "Adenine and Purine Nucleosides in Human Red Cell Preservation: A Review." Nov.-Dec. 1967, *Transfusion* 7:395-400.

The Free Online Medical Dictionary, 2012 (http://medical-dictionary.thefreedictionary.com/pyruvate).

U.S. Food and Drug Administration, "Anticoagulant Citrate Phosphate Double Dextrose (CP2D) & Additive Solution 3 (AS-3)—Summary Basis of Approval," [online, retrieved on Jun. 16, 2010]. Retrieved from the Internet: <URL: http://www.fda.gov/BiologicsBloodVaccines/BloodBloodProducts/ApprovedProducts/NewDrugApplicationsNDAs/ucm082820.htm>, 3 pgs.

Valeri et al., "Restoration in vivo of erythrocyte adenosine triphosphate, 2,3-diphosphoglycerate, potassium ion, and sodium ion concentrations following the transfusion of acid-citrate-dextrose-stored human red blood cells," *J. Lab. Clin. Med.*, May 1969; 73(5): 722-33.

Valeri et al., "The survival, function, and hemolysis of human RBCs stored at 4 degrees C in additive solution (AS-1, AS-3, or AS-5) for 42 days and then biochemically modified, frozen, thawed, washed, and stored at 4 degrees C in sodium chloride and glucose solution for 24 hours," *Transfusion*, Nov. 2000; 40(11):1341-5.

Vamvakas et al., "Length of storage of transfused red cells and postoperative morbidity in patients undergoing coronary artery bypass graft surgery," *Transfusion*, Jan. 2000; 40(1): 101-9.

van de Watering et al., "Effects of storage time ofred blood cell transfusions on the prognosis of coronary artery bypass graft patients," *Transfusion*, Oct. 2006; 46(10): 1712-8.

Walsh et al., "Does the storage time of transfused red blood cells influence regional or global indexes of tissue oxygenation in anemic critically ill patients?" *Crit. Care Med.*, Feb. 2004; 32(2): 364-71.

Zallen et al., "Age of transfused blood is an independent risk factor for postinjury multiple organ failure," *Am. J. Surg.*, Dec. 1999; 178(6): 570-2.

Zimmer, "Restitution of myocardial adenine nucleotides: acceleration by administration of ribose," *J. Physiol. (Paris)*, 1980; 76(7): 769-75.

Zimmer, "The oxidative pentose phosphate pathway in the heart: Regulation, physiological significance, and clinical implications," *Basic Res. Cardiol.*, Jul.-Aug. 1992; 87(4): 303-16.

\* cited by examiner

METHODS FOR TREATING RED BLOOD CELLS

This application is a continuation of U.S. patent application Ser. No. 13/028,819, filed Feb. 16, 2011, which claims the benefit of U.S. Provisional Application Nos. 61/338,299, filed Feb. 16, 2010, which are incorporated herein by reference in their entireties.

BACKGROUND

Whole blood is a living tissue that circulates through the heart, arteries, veins and capillaries, carrying nourishment, electrolytes, antibodies, heat and oxygen to the body tissues. Whole blood includes red blood cells (RBCs), white blood cells and platelets suspended in a proteinaceous fluid termed blood plasma. If blood is treated to prevent clotting and permitted to stand in a container, RBCs will settle to the bottom of the container, the plasma will remain on top and the white blood cells will form a layer on top of the RBCs. A centrifuge is commonly used to hasten this separation. The platelet-rich plasma is then removed and placed into a sterile bag for further processing to separate, for example, platelets, clotting factors, albumin, immunoglobulins and the like.

The most important component for the usual transfusion need are the erythrocytes or RBCs, which contain hemoglobin, a complex iron-containing protein that carries oxygen throughout the body and gives blood its red color. The percentage of blood volume that is composed of RBCs is called the "hematocrit." The average hematocrit in the adult male is 47%. There are about one billion RBCs in two or three drops of blood, and, for every 600 RBCs, there are about 40 platelets and one white blood cell.

Manufactured in the bone marrow, RBCs are enucleated, biconcave discs that are continuously being produced, broken down and destroyed. The biconcave disc shape is crucial to the function of RBCs, presenting a maximal surface area for the capture of oxygen in the lungs and its release in the tissue. The cells are flexible and able to bend in order to traverse the tiny tubules of the capillary beds. Since the cells are enucleated and lack mitochondria, they are unable to carry out cellular repair processes and must rely on anaerobic phosphorylation for energy. After an average of 120 days in the circulatory system, the cells are senescent and are phagocytized by circulating monocytes or the fixed macrophages of the reticuloendothelial system.

RBCs are prepared from whole blood by removing the plasma. When transfused into a patient, the hematocrit is raised while an increase in blood volume is minimized, which is especially important to such patients as those with congestive heart failure. The cells are typically suspended in about half the original volume; the preparation is referred to as packed red cells. Patients benefiting most from transfusions of RBCs include those with chronic refractive anemia from disorders such as kidney failure, malignancies, gastrointestinal bleeding or acute blood loss as from trauma or surgery.

Because patients seldom require all of the components of whole blood; it is the usual practice in blood banks to separate the blood into components and transfuse only that portion needed by the patient for a specific condition or disease. This treatment, referred to as "blood component therapy" allows several patients to benefit from each unit of blood. Unfortunately, the separation of blood components for therapy is detrimental to the RBCs, causing a storage lesion characterized by a decrease in the marker 2,3-diphosphoglycerate (2,3-DPG), an increase in the production of oxygen free radicals and a change in morphology.

Standard solutions for the storage of whole blood include citrate-phosphate-dextrose solution (CPD) and citrate-phosphate-dextrose-adenine solution (CPDA). Citrate or other anticoagulants such as heparin are necessary to prevent clotting. Because blood is a living tissue that maintains metabolic functions even at refrigerated temperatures, it has been considered necessary to provide an energy source such as dextrose. Phosphate ion can be used to buffer the lactate produced from dextrose utilization.

Improvements in cell preservation solutions over the last 15 years have increased the refrigerated shelf life of whole blood or RBCs from 21 to 42 days. After 42 days, the blood is discarded, since many of the cells have become senescent and would be immediately phagocytized upon transfusion into a recipient. Although the red cells may appear to survive in storage for five or six weeks, they rapidly develop storage lesions characterized by hemolysis and/or biochemical and biomechanical changes that can compromise their survival time and their ability to accept, transport, and unload oxygen to the tissue. For that reason, it is desirable to use the whole blood and blood products within three weeks or less of drawing.

The need remains for a solution in which blood cells in whole blood or packed red cell suspensions can be stored for an increased time and survive functionally when transfused into a recipient. The need also remains for a method to rejuvenate blood and RBCs which are functioning suboptimally.

SUMMARY

Methods of collecting and storing RBCs prior to transfusion continue to be a challenge in improving blood bank practice. RBCs can be stored for 42 days at 4° C., but over this time RBC storage lesions occur despite improvements of anticoagulant solutions and blood additives. Among the most significant storage lesions of RBCs are a) the depletion of 2,3-DPG, resulting in a decrease in the ability of the blood to offload oxygen to tissue leading to an increase in oxygen affinity; b) morphological changes that reduce cell viability, increase fragility, and decrease deformability, impacting the ability of the cell to traverse the microcirculation; and c) the release of biochemical substances that result in fever, cellular damage, and tissue dysfunction. These storage lesions predominantly result from the depletion of cellular energy (i.e., adenosine triphosphate, or ATP) and lactic acid accumulation associated with decreased energy metabolism.

Experimental additive solutions that slow the rate of 2,3-DPG depletion and ATP loss are known. See, for example, Dawson et al., *Prog Clin Biol Res.* 1985; 195:349-68; Dawson et al., *Transfusion* 1984 July-August; 24(4): 327-9; Dawson et al., *Hum Pathol.* 1983 March; 14(3):213-7; Dawson et al., *Transfusion* 1981 May-June; 21(3):285-90; and Dawson et al., *Transfusion* 1981 March-April; 21(2): 215. These experimental solutions typically include a series of inorganic phosphates and inosine. Although the solutions are capable of maintaining 2,3-DPG levels to some degree, the requirement of the solution constituents created some issues that limited their utility. One issue was the low solubility of inosine, which resulted in a slurry being added to the RBCs that would subsequently require washing the cells prior to transfusion. Another issue is the biochemical progression leading to the formation of the potentially toxic breakdown products such as hypoxanthine and uric acid. Furthermore, the transfusion product must be warmed for one hour prior to transfusion, which impacts the practicality of such an additive solution in current blood banking practice. In preferred embodiments, the blood storage and/or rejuvenating compositions disclosed herein address one or more of these issues.

In one aspect, the present disclosure provides a blood storage and/or rejuvenating composition. In one embodiment, the composition includes a nucleoside and D-ribose, with the proviso that the nucleoside is not inosine. In certain embodiments, the nucleoside includes one or more of adenosine, deoxyadenosine, guanosine, deoxyguanosine, 5'-methyluridine, thymidine, uridine, deoxyuridine, cytidine, and deoxycytidine. In preferred embodiments, the nucleoside is guanosine. Optionally, the composition can further include sodium pyruvate and/or inorganic phosphate. In certain embodiments the composition is an aqueous solution.

In another embodiment, the blood storage and/or rejuvenating composition includes 75 to 1500 mM guanosine. Optionally, the composition can further include D-ribose at a concentration of, for example, 75 to 1500 mM. Optionally, the composition can further include sodium pyruvate at a concentration of, for example, 75 to 1500 mM. Optionally, the composition can further include an inorganic phosphate at a concentration of, for example, 75 to 1500 mM. Optionally, the composition can further include L-arginine at a concentration of, for example, 75 to 1500 mM. Optionally, the composition can further include inosine at a concentration of, for example, 75 to 1500 mM. When used to store and/or rejuvenate blood, the composition is typically diluted approximately 30-fold to provide a final concentration of 2.5 to 50 mM guanosine; and optionally 2.5 to 50 mM D-ribose, 2.5 to 50 mM sodium pyruvate, 2.5 to 50 mM inorganic phosphate, 2.5 to 50 mM L-arginine, and/or 2.5 to 50 mM inosine.

In certain preferred embodiments, the blood storage and/or rejuvenating composition includes 150 to 900 mM guanosine. Optionally, the composition can further include D-ribose at a concentration of, for example, 150 to 900 mM. Optionally, the composition can further include sodium pyruvate at a concentration of, for example, 150 to 900 mM. Optionally, the composition can further include an inorganic phosphate at a concentration of, for example, 150 to 900 mM. Optionally, the composition can further include L-arginine at a concentration of, for example, 150 to 900 mM. Optionally, the composition can further include inosine at a concentration of, for example, 150 to 900 mM. When used to store and/or rejuvenate blood, the composition is typically diluted approximately 30-fold to provide a final concentration of 5 to 30 mM guanosine; and optionally 5 to 30 mM D-ribose, 5 to 30 mM sodium pyruvate, 5 to 30 mM inorganic phosphate, 5 to 30 mM L-arginine, and/or 5 to 30 mM inosine.

In other preferred embodiments, the blood storage and/or rejuvenating composition includes 300 to 600 mM guanosine. Optionally, the composition can further include D-ribose at a concentration of, for example, 300 to 600 mM. Optionally, the composition can further include sodium pyruvate at a concentration of, for example, 300 to 600 mM. Optionally, the composition can further include an inorganic phosphate at a concentration of, for example, 300 to 600 mM. Optionally, the composition can further include L-arginine at a concentration of, for example, 300 to 600 mM. Optionally, the composition can further include inosine at a concentration of, for example, 300 to 600 mM. When used to store and/or rejuvenate blood, the composition is typically diluted approximately 30-fold to provide a final concentration of 10 to 20 mM guanosine; and optionally 10 to 20 mM D-ribose, 10 to 20 mM sodium pyruvate, 10 to 20 mM inorganic phosphate, 10 to 20 mM L-arginine, and/or 10 to 20 mM inosine.

In another embodiment, the blood storage and/or rejuvenating composition includes: 225 mM guanosine; 300 mM D-ribose; 300 mM sodium pyruvate; and 300 mM inorganic phosphate. When used to store and/or rejuvenate blood, the composition is typically diluted approximately 30-fold to provide a final concentration of 7.5 mM guanosine, 10 mM D-ribose, 10 mM sodium pyruvate, and 10 mM inorganic phosphate.

The compositions described herein can be used, for example, in a method of storing blood. In certain embodiments, the method includes contacting RBCs with a blood storage and/or rejuvenating composition as described herein.

Alternatively, or in addition to, the compositions described herein can be used, for example, in a method of rejuvenating blood. In certain embodiments, the method includes contacting RBCs with a blood storage and/or rejuvenating composition as described herein.

Methods for storing and/or rejuvenating RBCs are described herein. Additional methods are described, for example, in U.S. Patent Application Publication No. 2007/0111191 A1 (St. Cyr et al.), U.S. Pat. No. 7,687,468 (St. Cyr et al.), and copending U.S. patent application Ser. No. 13/028,856, entitled "ARGININE-CONTAINING COMPOSITIONS AND METHODS FOR TREATING RED BLOOD CELLS", filed the same day herewith.

The technology described within this application describes a RBC storage and/or rejuvenating composition that, in preferred embodiments, does not present the solubility difficulties associated with inosine, does not produce a high level of breakdown products, and/or does not require warming of the RBCs prior to transfusion. The storage and/or rejuvenating composition described herein includes a pentose carbohydrate (e.g., D-Ribose) that can serve to aid de novo synthesis and metabolic salvage of purine nucleotides including ATP. The storage and/or rejuvenating composition can also include inorganic phosphate, which can serve as a substrate for phosphorolysis; and/or sodium pyruvate, which can serve as a source for NAD and allow 1,3-diphosphoglycerate to be converted to either 2,3-DPG or 3-phosphoglycerate. In one embodiment, guanosine can be used in place of inosine, which effectively can reduce the breakdown products produced by inosine, and can further enhance RBC ATP content. In another embodiment, L-arginine can be utilized to fully solubilize any inosine present.

Definitions

Unless otherwise specified, "a," "an," "the," and "at least one" are used interchangeably and mean one or more than one.

As used herein, the term "comprising," which is synonymous with "including" or "containing," is inclusive, open-ended, and does not exclude additional unrecited elements or method steps.

Also herein, the recitations of numerical ranges by endpoints include all numbers subsumed within that range (e.g., 1 to 5 includes 1, 1.5, 2, 2.75, 3, 3.80, 4, 5, etc.).

The above brief description of various embodiments of the present invention is not intended to describe each embodiment or every implementation of the present invention. Rather, a more complete understanding of the invention will become apparent and appreciated by reference to the following description and claims. Further, it is to be understood that other embodiments may be utilized and structural changes may be made without departing from the scope of the present invention.

DETAILED DESCRIPTION OF ILLUSTRATIVE EMBODIMENTS

In 1915, blood transfusion was first attempted from a direct donor to a recipient. During the years following World War I, the practice improved with the use of a citrate glucose solution to collect the blood, the use of refrigeration, and blood typing. Then, in the 1960's and 1970's, improvements continued when glass bottle storage was replaced with durable plastic bags, better anticoagulants were developed, and the addition of mannitol and adenine allowed for storage of RBCs for 42 days. See, for example, Bartlett et al., *J. Clin. Invest.* 1960; 39:56; Bunn et al., *J. Clin. Invest.* 1969; 48:311; Akerblom et al., *Scand. J. Clin. Lab. Invest.* 1968; 21:245-248; and Delivoria-Papadopoulos et al., *Science* 1969; 165:601-602. Today, blood is still preserved with various anticoagulant solutions that include adenine and citrate. The blood is stored at 4° C., collected in plasticized blood bags, and discarded if not used within 42 days because over this six week storage period RBC viability is largely lost. As RBCs die, the lysed cells release the more durable hemoglobin molecule, which has a low P50, and which presents a barrier to oxygen diffusion.

Today some estimate that there are approximately 16 million units of RBCs transfused annually in the United States. This number constitutes an average of 34,000 units used every day to support patients undergoing surgery (especially heart, liver, and kidney), cancer treatment, complications of sickle cell anemia, trauma, sepsis, and various conditions requiring critical care. Although several complications have been associated with RBC transfusion, the overall transfusion rate among patients in intensive care is reported to be 44% (Corwin et al., *Crit. Care Med.,* 2004; 32:39-52). Certain of the reported complications result from inherent properties of the blood products transfused, while others are a consequence of RBC storage.

RBCs undergo major biochemical and biomechanical changes during storage that affect their post transfusion performance and recent studies have drawn attention to possible adverse effects from older stored blood. See, for example, Walsh et al., *Crit. Care Med.* 2004; 32:364-371; Van de Watering et al., *Transfusion* 2006; 46:1712-1718; Vamvakas et al., *Transfusion* 2000; 40:101-109; and Hebert et al., *Anesthesia & Analgesia.* 2005; 100:1433-1438. The RBC storage lesion is evidenced by the loss of 2,3-DPG, the principal organic phosphate of the human erythrocyte. The 2,3-DPG content within the cell correlates with the position of the oxygen-hemoglobin dissociation curve, as reflected by the P50 (the partial pressure of oxygen at which hemoglobin is 50% saturated) in a variety of clinical conditions, including hypoxic states such as exposure to high altitude and cyanotic heart disease; a variety of anemia's; hyperthyroidism; septic shock; and the changes associated with blood storage (Oski et al., *Blood* 1971; 37:52-58). In blood stored under conventional blood bank conditions, the 2,3-DPG level drops sharply, and by 10 days of storage 2,3-DPG levels are only 20-25 percent of their original level. Within 21 days of storage they fall to 10 percent of their initial content (Van de Watering et al., *Transfusion* 2006; 46:1712-1718; and Vamvakas et al., *Transfusion* 2000; 40:101-109).

Storage lesions remain a significant concern and a major focus of research in transfusion medicine. Research evidence suggests that storage of RBCs for long periods of time results in reduced oxygen delivery, and transfusion of older blood (i.e., greater than 14-days of storage) has been identified as an independent risk factor for the development of multiple organ failure. See, for example, (Fitzgerald et al., *Crit. Care Med.* 1997; 25:726-732; Marik et al., JAMA, 1993; 269:3024-3029; Raat et al., *Crit. Care Med.,* 2005; 33:39-45; and Zallen et al., *Am. J. Surg.,* 1999; 178:570-572).

Based on the results of early studies (e.g., Van de Watering et al., *Transfusion* 2006; 46:1712-1718; and Vamvakas et al., *Transfusion* 2000; 40:101-109), it has been assumed that 2,3-DPG levels in RBCs are rejuvenated within 24-hours of transfusion. These studies were performed in normal volunteers with no circulatory problems and with normal blood volume. It is not known whether such recovery would occur in patients suffering from severe blood loss, circulatory issues, or problems associated with underlying medical conditions. Further, the inability of transfused RBCs to deliver oxygen to tissue during the critical time in the early hours following transfusion may have a significant impact on clinical outcome. Although certain studies indicate that the age of transfused RBCs has little or no effect on clinical outcomes in certain conditions (e.g., Hebert et al., *Anesthesia & Analgesia.* 2005; 100:1433-1438), others suggest the opposite, showing that the duration of storage of RBCs is associated with adverse outcome (Oski et al., *Blood* 1971; 37:52-58).

A predominance of the literature suggests the development of an RBC storage solution(s) that would limit or reverse storage lesions would be of considerable consequence to transfusion medicine and could help make RBC transfusion safer and more effective. See, for example, Fitzgerald et al., *Crit. Care Med.* 1997; 25:726-732; Marik et al., JAMA, 1993; 269:3024-3029; Raat et al., *Crit. Care Med.,* 2005; 33:39-45; Zallen et al., *Am. J. Surg.,* 1999; 178:570-572; Buetler et al., *J. Lab. Clin. Med.,* 1969; 74:300; and Valerie et al., *J. Lab. Clin. Med.,* 1969; 73:722-733. It is postulated that presently disclosed RBC storage and/or rejuvenating compositions will provide such a restorative benefit.

In one aspect, the present disclosure provides a blood storage and/or rejuvenating composition. In one embodiment, the composition includes a nucleoside and D-ribose, with the proviso that the nucleoside is not inosine. In certain embodiments, the nucleoside includes one or more of adenosine, deoxyadenosine, guanosine, deoxyguanosine, 5'-methyluridine, thymidine, uridine, deoxyuridine, cytidine, and deoxycytidine. In preferred embodiments, the nucleoside is guanosine. Optionally, the composition can further include sodium pyruvate and/or inorganic phosphate. In certain embodiments the composition is an aqueous solution. In preferred embodiments, the composition is an aqueous composition having a pH of 6 to 8.5.

In another embodiment, the blood storage and/or rejuvenating composition includes 75 to 1500 mM guanosine. Optionally, the composition can further include D-ribose at a concentration of, for example, 75 to 1500 mM. Optionally, the composition can further include sodium pyruvate at a concentration of, for example, 75 to 1500 mM. Optionally, the composition can further include an inorganic phosphate at a concentration of, for example, 75 to 1500 mM. Optionally, the composition can further include L-arginine at a concentration of, for example, 75 to 1500 mM. Optionally, the composition can further include inosine at a concentration of, for example, 75 to 1500 mM. When used to store and/or rejuvenate blood, the composition is typically diluted approximately 30-fold to provide a final concentration of 2.5 to 50 mM guanosine; and optionally 2.5 to 50 mM D-ribose, 2.5 to 50 mM sodium pyruvate, 2.5 to 50 mM inorganic phosphate, 2.5 to 50 mM L-arginine, and/or 2.5 to 50 mM inosine.

In certain preferred embodiments, the blood storage and/or rejuvenating composition includes 150 to 900 mM guanosine. Optionally, the composition can further include D-ribose at a concentration of, for example, 150 to 900 mM. Optionally, the composition can further include sodium pyruvate at a concentration of, for example, 150 to 900 mM. Optionally, the composition can further include an inorganic phosphate at a concentration of, for example, 150 to 900 mM. Optionally, the composition can further include L-arginine at a concentration of, for example, 150 to 900 mM. Optionally, the composition can further include inosine at a concentration of, for example, 150 to 900 mM. When used to store and/or rejuvenate blood, the composition is typically diluted approximately 30-fold to provide a final concentration of 5 to 30 mM guanosine; and optionally 5 to 30 mM D-ribose, 5 to 30 mM sodium pyruvate, 5 to 30 mM inorganic phosphate, 5 to 30 mM L-arginine, and/or 5 to 30 mM inosine.

In other preferred embodiments, the blood storage and/or rejuvenating composition includes 300 to 600 mM guanosine. Optionally, the composition can further include D-ribose at a concentration of, for example, 300 to 600 mM. Optionally, the composition can further include sodium pyruvate at a concentration of, for example, 300 to 600 mM. Optionally, the composition can further include an inorganic phosphate at a concentration of, for example, 300 to 600 mM. Optionally, the composition can further include L-arginine at a concentration of, for example, 300 to 600 mM. Optionally, the composition can further include inosine at a concentration of, for example, 300 to 600 mM. When used to store and/or rejuvenate blood, the composition is typically diluted approximately 30-fold to provide a final concentration of 10 to 20 mM guanosine; and optionally 10 to 20 mM D-ribose, 10 to 20 mM sodium pyruvate, 10 to 20 mM inorganic phosphate, 10 to 20 mM L-arginine, and/or 10 to 20 mM inosine.

In another embodiment, the blood storage and/or rejuvenating composition includes: 225 mM guanosine; 300 mM D-ribose; 300 mM sodium pyruvate; and 300 mM inorganic phosphate. When used to store and/or rejuvenate blood, the composition is typically diluted approximately 30-fold to provide a final concentration of 7.5 mM guanosine, 10 mM D-ribose, 10 mM sodium pyruvate, and 10 mM inorganic phosphate.

The compositions described herein can be used, for example, in a method of storing blood. In certain embodiments, the method includes contacting RBCs with a blood storage and/or rejuvenating composition as described herein.

Alternatively, or in addition to, the compositions described herein can be used, for example, in a method of rejuvenating blood. In certain embodiments, the method includes contacting RBCs with a blood storage and/or rejuvenating composition as described herein.

In certain preferred embodiments, the method of rejuvenating blood includes: providing RBCs (e.g., packed RBCs or in whole blood) having a 2,3-DPG value lower than the value for freshly drawn blood; and mixing the RBCs with a blood storage and/or rejuvenating composition under conditions effective to increase the 2,3-DPG value, wherein the blood storage and/or rejuvenating composition includes guanosine. In certain embodiments, conditions effective to increase the 2,3-DPG value include incubating the cells in the blood storage and/or rejuvenating composition at a temperature of 4° C. to 37° C., and in certain preferred embodiments at a temperature of room temperature. In certain embodiments, conditions effective to increase the 2,3-DPG value include incubating the cells in the blood storage and/or rejuvenating composition for a time of at least 10 minutes, in preferred embodiments for a time of 10 minutes to 48 hours, in certain preferred embodiments for a time of 10 minutes to 4 hours, and in other preferred embodiments for a time of 30 minutes to 2 hours. Exemplary conditions effective to increase the 2,3-DPG value include incubating the cells in the blood storage and/or rejuvenating composition at 37° C. for 10 minutes to four hours. Other exemplary conditions effective to increase the 2,3-DPG value include incubating the cells in the blood storage and/or rejuvenating composition at room temperature for 10 minutes to four hours. In preferred embodiments, the blood storage and/or rejuvenating composition includes one or more of the blood storage and/or rejuvenating compositions described herein.

In certain preferred embodiments, the method of rejuvenating blood includes: providing RBCs (e.g., packed RBCs or in whole blood) having an ATP value lower than the value for freshly drawn blood; and mixing the RBCs with a blood storage and/or rejuvenating composition under conditions effective to increase the ATP value, wherein the blood storage and/or rejuvenating composition includes guanosine. In certain embodiments, conditions effective to increase the ATP value include incubating the cells in the blood storage and/or rejuvenating composition at a temperature of 4° C. to 37° C., and in certain preferred embodiments at a temperature of room temperature. In certain embodiments, conditions effective to increase the ATP value include incubating the cells in the blood storage and/or rejuvenating composition for a time of at least 10 minutes, in preferred embodiments for a time of 10 minutes to 48 hours, in certain preferred embodiments for a time of 10 minutes to 4 hours, and in other preferred embodiments for a time of 30 minutes to 2 hours. Exemplary conditions effective to increase the ATP value include incubating the cells in the blood storage and/or rejuvenating composition at 37° C. for 10 minutes to four hours. Other exemplary conditions effective to increase the ATP value include incubating the cells in the blood storage and/or rejuvenating composition at room temperature for 10 minutes to four hours. In preferred embodiments, the blood storage and/or rejuvenating composition includes one or more of the blood storage and/or rejuvenating compositions described herein.

By increasing 2,3-DPG concentration in stressed RBCs, it is postulated RBC storage and/or rejuvenating compositions as disclosed herein will decrease oxygen affinity and increase oxygen delivery to affected tissue following transfusion. Further, by maintaining cellular energetics, it is hypothesized that the storage and/or rejuvenating compositions disclosed herein will decrease cell fragility and increase deformability, thereby improving flow through the capillaries. The net result will be a decrease in storage lesions and greater oxygen delivery to affected tissue following transfusion.

The present invention is illustrated by the following examples. It is to be understood that the particular examples, materials, amounts, and procedures are to be interpreted broadly in accordance with the scope and spirit of the invention as set forth herein.

EXAMPLES

Example 1

A storage and/or rejuvenating composition that includes D-ribose, inosine, sodium pyruvate, and inorganic phosphate, all at a 300 mM concentration as a slurry was prepared. When used to store and/or rejuvenate RBCs, the slurry is diluted 30-fold to a final concentration of 10 mM to form a solution. The composition exhibits significant results in restoring 2,3-DPG levels in stored RBCs and increasing the ATP content from the baseline value. In a study, RBCs were collected and stored for an average of 21 days at 4° C. according to standard blood banking practice. Various RBC storage and/or rejuvenating compositions were added to the 21-day old stored RBCs and held at 37° C. for one to four hours before being tested for 2,3-DPG concentrations. 2,3-DPG levels were measured in all the examples using a diagnostic 2,3-diphosphoglycerate (DPG) kit available from Roche Diagnostics Corp. (Cat. #10148334001). A normal 2,3-DPG concentration of RBC immediately upon harvest is 4.0 μmol/ml. Following storage the average 2,3-DPG concentration fell to 0.17 μmol/ml (Table 1). The addition of RBC storage and/or rejuvenating composition restored the concentration to greater than 50% of normal post-harvest level. An increase to 1.0 μmol/ml is considered a significant improvement. This series of experiments demonstrated a RBC storage and/or rejuvenating composition increased ATP content and 2,3-DPG levels. The practicality of the solution for adoption in blood bank practice may be limited, however, due to the low solubility of inosine as well as the need for warming of the blood (e.g., for one hour) prior to transfusion.

TABLE 1

2,3-DPG Level of Stored RBCs with RBC Storage and/or Rejuvenating Composition

| Time Point (Hours) | Average 2,3-DPG (μmol/ml) | Range (μmol/ml) | N = | % ATP increase |
|---|---|---|---|---|
| 0 | 0.17 | 0.07-0.35 | 5 | |
| 1 | 2.4 | 1.8-3.3 | 10 | 24 |
| 2 | 1.8 | 1.2-2.7 | 10 | 22 |

Experimental protocols were designed to find methods to increase the solubility of inosine. It was found that L-arginine in an equimolecular solution enhanced the inosine solubility such that inosine remained in solution at concentrations above 50 mM at room temperature. A storage and/or rejuvenating composition including 300 mM each of inosine, L-arginine, sodium pyruvate, D-ribose, and inorganic phosphate was diluted 30-fold into 21-day old stored RBCs. One set of stored blood samples was incubated for 60 minutes at room temperature and another was incubated for 60 minutes at 37° C. As shown in Table 2, the L-arginine containing storage and/or rejuvenating compositions successfully restored 2,3-DPG and ATP levels regardless of mode of warming. This result demonstrates the rejuvenation of 2,3-DPG and ATP using room temperature incubation and a solution devoid of problems associated with slurries and washing of the red cells prior to transfusion.

TABLE 2

2,3-DPG and ATP of stored RBC in L-arginine containing solution

| Sample | Average 2,3-DPG (μmol/ml) | Range (μmol/ml) | N = | % ATP increase |
|---|---|---|---|---|
| Control | 0.29 | N.A. | 1 | |
| 60 minutes at 37° C. | 3.2 | 2.9-3.5 | 3 | 29 |
| 60 minutes at Room Temperature | 1.3 | 1.0-1.5 | 3 | 27 |

Example 2

An additional experimental protocol was designed to determine if nucleosides other than inosine can successfully aid in restoring 2,3-DPG and ATP levels and, potentially, reduce formation of the breakdown products, hypoxanthine and uric acid. Guanosine, a purine nucleoside consisting of guanine linked by its N9 nitrogen to the C1 carbon of ribose, was chosen as the test nucleotide. Table 3 presents data obtained using a storage and/or rejuvenating composition including a 10 mM final concentration each of guanosine, sodium pyruvate, inorganic phosphate, and D-ribose.

TABLE 3

2,3-DPG and ATP of stored RBC in a guanosine containing solution

| Time Point (Hours) | Average 2,3-DPG (μmol/ml) | Range (μmol/ml) | N = | % ATP increase |
|---|---|---|---|---|
| Control | 0.25 | N.A. | 1 | |
| 60 minutes at 37° C. | 1.94 | 1.51-2.43 | 3 | 43 |
| 60 minutes at Room Temperature | 0.51 | 0.28-0.83 | 3 | 32 |

The 10 mM guanosine solution was capable of restoring 2,3-DPG levels when heated to 37° C. for 60 minutes. The concentrated guanosine composition was not completely soluble and, upon dilution, did not restore 2,3-DPG levels following room temperature incubation, although ATP levels were elevated.

Example 3

Table 4 presents data obtained using a storage and/or rejuvenating composition including 10 mM each of inorganic phosphate and D-ribose, and guanosine at the indicated concentration. The solutions did not include sodium pyruvate. Rejuvenation was observed for 60 minutes incubation at 37° C.

TABLE 4

| | 2,3-DPG (μmol/ml) |
|---|---|
| Control | 0.20 |
| 1 mM Guanosine | 0.47 |
| 5 mM Guanosine | 1.30 |
| 10 mM Guanosine | 1.10 |

Example 4

Table 5 presents data obtained using a storage and/or rejuvenating composition including a final concentration of 10 mM each of L-arginine, inosine, D-ribose, sodium pyruvate, and inorganic phosphate. Rejuvenation was observed after 10 minutes and 60 minutes of incubation at 37° C.

TABLE 5

| | 2,3-DPG (µmol/ml) |
|---|---|
| Control | −0.17 |
| 10 minutes at 37° C. | 1.39 |
| 60 minutes at 37° C. | 4.25 |

Example 5

Rejuvenation was not observed for 60 minutes incubation at 37° C. when inosine was replaced with varying concentrations of inosine monophosphate in a storage and/or rejuvenating composition including 10 mM each of D-ribose, sodium pyruvate, and inorganic phosphate.

Example 6

Rejuvenation was not observed for 60 minutes incubation at 37° C. when inosine was replaced with varying concentrations of ribose-5-phosphate in a storage and/or rejuvenating composition including 10 mM each of D-ribose, sodium pyruvate, and inorganic phosphate.

Example 7

Rejuvenation was not observed for 10 minutes incubation at 4° C. in a storage and/or rejuvenating composition including 10 mM each of inosine, D-ribose, sodium pyruvate, and inorganic phosphate.

The complete disclosure of all patents, patent applications, and publications, and electronically available material (e.g., GenBank amino acid and nucleotide sequence submissions; and protein data bank (pdb) submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of storing blood, the method comprising:
   contacting red blood cells with a blood storage composition effective to maintain a normal physiological level of 2,3-diphosphoglycerate (2,3-DPG) and reduce time-related decrease in ATP in the red blood cells, the composition comprising:
   D-ribose; and
   a nucleoside other than inosine.

2. The method of claim 1 wherein the red blood cells are packed red blood cells or in whole blood.

3. The method of claim 1, wherein the nucleoside is guanosine.

4. The method of claim 1, wherein the red blood cells are contacted with the blood storage composition at a temperature of 4° C. to 37° C.

5. A method of rejuvenating blood, the method comprising contacting red blood cells with a blood rejuvenating composition effective to produce a normal physiological level of 2,3-diphosphoglycerate (2,3-DPG) and reduce time-related decrease in ATP in the red blood cells, the composition comprising:
   D-ribose; and
   a nucleoside other than inosine.

6. The method of claim 5 wherein the red blood cells are packed red blood cells or in whole blood.

7. The method of claim 5, wherein the nucleoside is guanosine.

8. The method of claim 5, wherein the red blood cells are contacted with the blood rejuvenating composition at a temperature of 4° C. to 37° C.

9. A method of rejuvenating blood, the method comprising:
   providing red blood cells having a 2,3-diphosphoglycerate value lower than the value for freshly drawn blood; and
   mixing the red blood cells with a blood rejuvenating composition under conditions effective to increase the 2,3-diphosphoglycerate value,
   wherein the blood rejuvenating composition comprises guanosine in an amount effective to increase the 2,3-diphosphoglycerate value to a normal physiological level and reduce time-related decrease in ATP.

10. The method of claim 9 wherein conditions effective comprise incubating the cells in the blood rejuvenating composition at a temperature of 4° C. to 37° C.

11. The method of claim 10 wherein the temperature is room temperature.

12. The method of claim 9 wherein conditions effective comprise incubating the cells in the blood rejuvenating composition for a time of at least 10 minutes.

13. The method of claim 12 wherein the time is 10 minutes to 48 hours.

14. The method of claim 13 wherein the time is 10 minutes to 4 hours.

15. The method of claim 14 wherein the time is 30 minutes to 2 hours.

16. The method of claim 9 wherein the rejuvenating composition further comprises D-ribose.

17. The method of claim 9 wherein the red blood cells are packed red blood cells or in whole blood.

18. The method of claim 9, wherein the conditions effective to increase the 2,3-diphosphoglycerate value comprise a temperature of 4° C. to 37° C.

19. A method of rejuvenating blood, the method comprising:
   providing red blood cells having an adenosine triphosphate value lower than the value for freshly drawn blood; and
   mixing the red blood cells with a blood rejuvenating composition under conditions effective to increase the adenosine triphosphate value and reduce time-related decrease in ATP, the blood rejuvenating composition comprising D-ribose and guanosine.

20. The method of claim 19, wherein the conditions effective to increase the adenosine triphosphate value comprise a temperature of 4° C. to 37° C.

* * * * *